United States Patent [19]
Thottathil et al.

[11] Patent Number: 5,298,625
[45] Date of Patent: Mar. 29, 1994

[54] PROCESS FOR THE PREPARATION OF 4-PHOSPHINYL-3-KETO-CARBOXYLATE AND 4-PHOSPHONYL-3-KETO-CARBOXYLATE INTERMEDIATES USEFUL IN THE PREPARATION OF PHOSPHORUS CONTAINING HMG-COA REDUCTASE INHIBITORS

[75] Inventors: John K. Thottathil, Robbinsville; Wen S. Li, Lincroft, both of N.J.

[73] Assignee: E. R. Squibb & Sons, Inc., Princeton, N.J.

[21] Appl. No.: 987,514

[22] Filed: Dec. 7, 1992

[51] Int. Cl.$^5$ .................. C07F 7/02; C07F 9/02
[52] U.S. Cl. ........................... 548/406; 548/414
[58] Field of Search .............. 548/414, 406; 558/125, 558/179; 562/24

[56] References Cited

FOREIGN PATENT DOCUMENTS 319479 6/1989 European Pat. Off. ............ 548/514
319482 6/1989 European Pat. Off. ............ 548/514

OTHER PUBLICATIONS

T. Azuhata et al., "Synthesis of Diethyl 2-(Trimethylsiloxy)alkanephosphonates from Epoxides and Diethyl Trimethylsilyl Phosphite", *Communications*, 1983; 916–917.
S. Racha et al., "A Facile Synthesis of β-and γ-Hydroxyphosphonate Esters From Epoxides", *Tet. Lett.*, 1992; 33:5491–5494.
T. Azuhata et al., "Synthesis of Dialkyl 2-(Dialkoxyphosphoinyloxy)alkanephosphonates", *Communications*, 1984:417–418.

(List continued on next page.)

Primary Examiner—Mary C. Lee
Assistant Examiner—Joseph K. McKane
Attorney, Agent, or Firm—Ellen K. Park

[57] ABSTRACT

A process for the preparation of compounds of formula

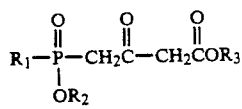

I or salt thereof where
$R_1$ is —X—Z and X is —C≡C—,
$R_2$ and $R_2'$ are independently hydrogen, alkyl or trialkylsilyl;
$R_3$ is hydrogen or alkyl; and
Z is a hydrophobic anchor;

which includes reacting a compound of formula

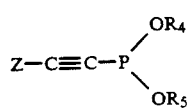

II where $R_4$ is alkyl, cycloalkyl or aryl; and $R_5$ is trialkylsilyl or triarylsilyl with a compound of formula

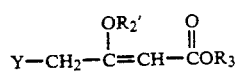

III where Y is a halogen, to form a compound of formula

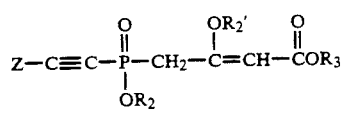

IV and hydrolyzing the compound of formula IV to obtain the compounds of formula I. Compounds of formula I or salt thereof where $R_1$ is —$OR_2'$ may be prepared by reacting a compound of formula III with a compound of formula $P(OR_2)_3$    XII.

2 Claims, No Drawings

PROCESS FOR THE PREPARATION OF 4-PHOSPHINYL-3-KETO-CARBOXYLATE AND 4-PHOSPHONYL-3-KETO-CARBOXYLATE INTERMEDIATES USEFUL IN THE PREPARATION OF PHOSPHORUS CONTAINING HMG-COA REDUCTASE INHIBITORS

FIELD OF THE INVENTION

This invention relates to a process for the preparation of intermediates useful in the preparation of compounds which inhibit the activity of 3-hydroxy-3-methylglutaryl coenzyme A (HMG-CoA) reductase. The instant invention also relates to the novel intermediates produced.

BRIEF DESCRIPTION OF THE INVENTION

The instant invention provides a process for the preparation of compounds of formula

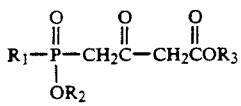   I and pharmaceutically acceptable salts thereof.

As used in formula I and throughout the specification, the symbols have the following meanings:

$R_1$ is —X—Z or —$OR_2'$;

$R_2$ and $R_2'$ are independently hydrogen, alkyl or trialkylsilyl;

$R_3$ is hydrogen or alkyl;

X is —$CH_2$—, —$CH_2CH_2$—, —$CH_2CH_2CH_2$—, —CH=CH—, —C≡C— or —$CH_2O$—, (where O is linked to Z); and Z is a hydrophobic anchor (as defined in U.S. Pat. No. 5,091,378, the disclosure of which is incorporated by reference herein).

Compounds of the formula I are useful as intermediates in the preparation of HMG-CoA reductase inhibitors, which are useful for example, in the treatment of hypercholesterolemia, hyperlipoproteinemia, hyperlipodemia and atherosclerosis. The instant invention provides a convenient process for the preparation of compounds of formula I in good yields.

DETAILED DESCRIPTION OF THE INVENTION

Listed below are definitions of various terms used to describe this invention. These definitions apply to the terms as they are used throughout the specification (unless they are otherwise limited in specific instances) either individually or as part of a larger group.

The term "alkyl" includes both straight and branched chain hydrocarbons, containing 1 to 12 carbon atoms in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl serityl, nonyl, decyl, undecyl, dodecyl, the various branched chain isomers thereof, and the like as well as substituted groups, including the following substituents: halo, alkoxy, aryl, alkylaryl, haloaryl, cycloalkyl, alkylcycloalkyl, hydroxy, alkylamine, alkanoylamino, nitro, cyano, thiol or alkylthio.

The term "lower alkyl" includes an alkyl group as described above having from 1 to 6, most preferably 1 to 4 carbon atoms.

The terms "alkenyl" and "alkynyl" include both straight and branched chain groups. Those groups having 2 to 10 carbon atoms are preferred.

The term "cycloalkyl" includes saturated cyclic hydrocarbon groups containing 3 to 12 carbons, preferably 3 to 8 carbons, which include cyclopropyl, cyclobutyl, and the like, any of which groups may be substituted with halogens, alkyl, alkoxy, hydroxy and the like.

The term "alkoxy" or "lower alkoxy" includes an alkyl or lower alkyl group linked to an oxygen atom.

The term "aryl" refers to phenyl and substituted phenyl. "Substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl, or carboxy groups. Exemplary substituted phenyl groups are substituted with 1, 2 or 3 amino, alkylamino, dialkylamino, nitro, halogen, hydroxyl, trifluoromethyl, alkyl (of 1 to 4 carbon atoms), alkoxy (of 1 to 4 carbon atoms) alkanoyloxy, carbamoyl or carboxyl groups.

The term "alkanoyl" as used herein refers to an alkyl group linked to a carbonyl group.

The term "halogen" or "halo" includes fluorine, chlorine, bromine and iodine. The term "salt(s)" refers to acidic and/or basic salts formed with inorganic and organic acids and bases. Basic salts are preferred. Exemplary basic salts include ammonium salts, alkali metal salts such as lithium, sodium and potassium salts (which are preferred), alkaline earth metal salts such as the calcium and magnesium salts, salts with organic bases, for example, amine salts such as dicyclohexylamine salt, benzathine, N-methyl-D-glucamine, salts with amino acids such as arginine and lysine and equivalent such salts. The nontoxic, pharmaceutically acceptable salts are preferred, although other salts are also useful, for example, in isolation or purification steps which may be employed during preparation.

The process for the preparation of compounds of formula I, where $R_1$ is —X—Z and X is —C≡C—, comprises the steps of:

(A) reacting a compound of formula

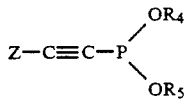   II where $R_4$ is alkyl, cycloalkyl or aryl and $R_5$ is trialkylsilyl or triarylsilyl with a compound of formula

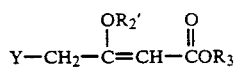   III where Y is a halogen, to form a compound of formula

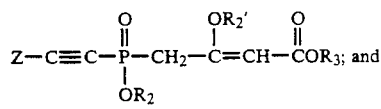   IV (B) hydrolyzing the product of step (A) to obtain the compounds of formula I.

The starting materials of formula II are prepared by deprotonating a compound of formula

   V with a base such as n-butyllithium, lithium hexamethyldisilazide or lithium diisopropylamide in an organic solvent such as tetrahydrofuran, toluene or heptane to form the acetylides of formula

   VI where M is an alkali metal such as sodium, lithium or potassium; and treating the acetylides with a (R$_4$)$_2$halophosphite such as diethylchlorophosphite to form the intermediates of formula

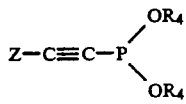   VII

Quenching the reaction mixture that contains the intermediates of formula VII with an aqueous solution of an organic or inorganic base such as saturated sodium bicarbonate, triethylamine or potassium bicarbonate followed by extractive work-up and controlled hydrolysis in the presence of a catalytic amount of acid such as p-toluenesulfonic acid provides the compounds of formula

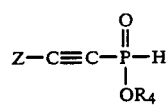   VIII which are then silylated with a silylating agent such as trimethylsilyl chloride, trimethylsilyl bromide, trimethylsilyl iodide, tert-butyldimethylsilyl chloride, tert-butyldiphenylsilyl chloride, N,N-diethyl-trimethylsilylamine, N,O-bis(trimethylsilyl)acetamide and N,O-bis-(trimethylsilyl)trifluoroacetamide in an organic solvent such as tetrahydrofuran, toluene, or heptane to provide the formula II compounds.

Compounds of formula V, may be prepared by methods disclosed in U.S. Pat. No. 5,091,378 cited above. Alternatively, compounds of formula V may be prepared by:

(1) reacting compounds of formula

   IX with an alkylating agent such as carbon tetrachloride or carbon tetrabromide and a reducing agent such as triethylphosphite in an inert organic solvent such as methylene chloride, 1,2-dichloroethane or acetonitrile at temperatures from about −20° C. to about −40° C. to form compounds of formula

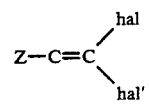   X where hal and hal' are the same or different halogen, and (2) reacting the product of step (1) with a base such as sodium ethoxide, sodium methoxide, potassium t-butoxide or potassium t-amylate or similar bases in the presence of a reducing agent such as diethylphosphite or dimethylphosphite or similar phosphites to form the compounds of formula V.

The starting material of formula IX may be prepared by the skilled artisan; for example, as disclosed in U.S. Pat. No. 5,091,378.

Compounds of formula III, where Y is bromine and R$_3$ is ethyl are commercially available. Compounds of formula III, where Y is other than bromine can be prepared from the commercially available corresponding ketones of formula

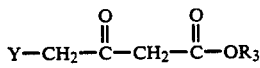   XI by reacting the ketones with a silylating agent such as trimethylsilylchloride or triethylorthoformate. Where Y is iodine, the compounds may be prepared from the corresponding chloride compounds, which are commercially available.

Compounds of formula I, where R$_1$ is —OR$_2'$ may be prepared by reacting compounds of formula III with a compound of formula

P(OR$_2$)$_3$   XII.

Compounds of formula XII are commercially available.

All stereoisomers of the compounds of the instant invention are contemplated, either in admixture or in pure or substantially pure form.

Although the procedures above have been described for the preparation of compounds of formula I, where X is —C≡C—, compounds of formula I where X is —CH$_2$—, —CH$_2$CH$_2$—, —CH$_2$CH$_2$CH$_2$—, —CH═CH— or —CH$_2$O— (where O is linked to Z) may be prepared by modifying the procedures described herein by a skilled artisan.

Preferred compounds of the formula I are those where R$_1$ is —X—Z and X is —C≡C—, and Z is

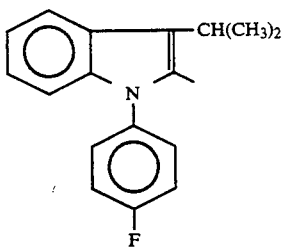

and R$_2$ and R$_3$ are lower alkyl or where R$_1$ is —OR$_2'$ and R$_2'$, R$_2$ and R$_3$ are lower alkyl.

The compounds of the formula I, prepared as described herein may be employed in the preparation of inhibitors of the enzyme HMG-CoA reductase. Exemplary such inhibitors, and methods of preparation thereof, are described in U.S. Pat. No. 5,091,378.

It is particularly preferred to prepare HMG-CoA reductase inhibitors of the formula

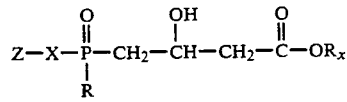   XIII wherein

R is hydroxy or lower alkoxy;

R$_x$ is hydrogen or lower alkyl,

X is —CH$_2$—, —CH$_2$CH$_2$—, —CH$_2$CH$_2$CH$_2$—, —CH=CH—, —C≡C—, or —CH$_2$O—, (where O is linked to Z); and Z is a hydrophobic anchor or salts thereof, which compounds and processes of forming such compounds using the starting materials of formula I where R$_1$ is —X—Z, are described in U.S. Pat. No. 5,091,378.

Examples of such compounds of formula XIII include (S)-4-[[[1-(4-fluorophenyl)-3-(1-methylethyl)-1H-indol-2-yl]ethynyl]hydroxyphosphinyl]-3-hydroxybutanoic acid, or its sodium salt (SQ 33,600) (preferred) or its dilithium salt;

4-[[[1-(4-Fluorophenyl)-3-(1-methylethyl)-1H-indol-2-yl]ethynyl]hydroxylphosphinyl]-3-hydroxybutanoic acid, ethyl ester, 1-adamantanamine (1:1) salt;

(S)-4-[[(E)-2-[4'-fluoro-3,3',5-trimethyl-[1,1'-biphenyl]-2-yl]ethenyl]hydroxy-phosphinyl]-3-hydroxybutanoic acid or its dilithium salt;

(S)-4-[[2-[4'-fluoro-3,3',5-trimethyl[1,1'-biphenyl]-2-yl]ethyl]hydroxyphosphinyl]-3-hydroxybutanoic acid, methyl ester or mono- or dialkali metal salts thereof;

(S)-4-[[[4'-fluoro-3,3',5-trimethyl[1,1'-biphenyl]-2-yl]ethynyl]methoxyphosphinyl]-3-hydroxybutanoic acid or the methyl ester thereof;

(5Z)-4-[[2-[4'-fluoro-3,3',5-trimethyl[1,1'-biphenyl]-2-yl]ethenyl]hydroxyphosphinyl]-3-hydroxybutanoic acid, methyl ester thereof;

(S)-4-[[2-[3-(4-fluorophenyl)-1-(1-methyl-ethyl)-1H-indol-2-yl]ethyl]methoxy-phosphinyl]-3-hydroxybutanoic acid, methyl ester;

(S)-4-[[2-[[1,1'-biphenyl]-2-yl]ethyl]-methoxyphosphinyl-3-hydroxybutanoic acid, methyl ester;

(S)-4-[[2-[4'-fluoro-3,3',5-trimethyl[1,1'-biphenyl]-2-yl]ethyl]hydroxyphosphinyl]-3-hydroxybutanoic acid, dilithium salt;

(S)-4-[[2-[4'-fluoro-3,3',5-trimethyl[1,1'-biphenyl]-2-yl]ethynyl]hydroxyphosphinyl]-3-hydroxybutanoic acid, dilithium salt;

(SZ)-4-[[2-[4'-fluoro-3,3',5-trimethyl[1,1'-biphenyl]-2-yl]ethenyl]hydroxyphosphinyl]-3-hydroxybutanoic acid, dilithium salt;

(S)-4-[[2-[3-(4-fluorophenyl)-1-(1-methylethyl)-1H-indol-2-yl]ethyl]hydroxyphosphinyl]-3-hydroxybutanoic acid, dilithium salt;

(S)-4-[[2-[(1,1'-biphenyl]-2-yl]ethyl]-hydroxyphosphinyl]-3-butanoic acid, dilithium salt;

(S)-4-(hydroxymethoxyphosphinyl)-3-[[(1,1-dimethylethyl)diphenylsilyl]oxy]butanoic acid, methyl ester, or its dicyclohexylamine (1:1) salt;

(E)-4-[[2-[3-(4-fluorophenyl)-1-(1-methylethyl)-1H-indol-2-yl]ethenyl]hydroxyphosphinyl]-3-hydroxybutanoic acid or its dilithium salt or methyl ester thereof;

4-[[2-[4'-fluoro-3,3',5-trimethyl[1,1'-biphenyl]-2-yl]ethyl]hydroxyphosphinyl]-3-hydroxybutanoic acid or its dilithium salt or methyl ester thereof;

(E)-4-[[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;

(S)-4-[[[2,4-dimethyl-6-[(4-fluorophenyl)methoxy]-phenyl]ethyl]hydroxyphosphinyl]-3-hydroxybutanoic acid or its dilithium salt or methyl ester thereof;

(S)-4-[[[2,4-dimethyl-6-[(4-fluorophenyl)methoxy]-phenyl]ethynyl]hydroxyphosphinyl]-3-hydroxybutanoic acid or its dilithium salt or methyl ester thereof;

(S)-4-[[2-[3,5-dimethyl[1,1'-biphenyl]-2-yl]ethyl]hydroxyphosphinyl]-3-hydroxybutanoic acid or its dilithium salt or methyl ester thereof;

(S)-4-[[2-[4'-fluoro-3,5-dimethyl[1,1'-biphenyl]-2-yl]ethyl]hydroxyphosphinyl]-3-hydroxybutanoic acid or its dilithium salt or methyl ester thereof;

(S)-4-[[2-[[1,1'-biphenyl]-2-yl]ethynyl]-hydroxyphosphinyl]-3-hydroxybutanoic acid or its dilithium salt or methyl ester thereof;

(S)-4-[[2-(5-(4-fluorophenyl)-3-(1-methylethyl)-1-phenyl-1H-pyrazol-4-yl]ethynyl]methoxyphosphinyl]-3-hydroxybutanoic acid, methyl ester;

(S)-4-[[2-[1-(4-fluorophenyl)-3-(1-methylethyl)-1-indol-2-yl]ethynyl]hydroxyphosphinyl]-3-hydroxybutanoic acid or its dilithium salt or disodium salt or methyl ester thereof;

(S)-4-[[2-[1-(4-fluorophenyl)-3-(1-methylethyl)-1H-indol-2-yl]ethyl]hydroxyphosphinyl]-3-hydroxybutanoic acid or its dilithium salt or methyl ester thereof;

(S)-4-[[2-[5-(4-fluorophenyl)-3-(1-methylethyl)-1-phenyl-1H-pyrazol-4-yl]ethynyl]hydroxyphosphinyl]-3-hydroxybutanoic acid, dilithium salt;

(E)-4-[[2-[5-(4-fluorophenyl)-3-(1-methylethyl)-1-phenyl-1H-pyrazol-4-yl]ethenyl]-methoxyphosphinyl]-3-hydroxybutanoic acid, methyl ester;

(E)-4-[[2-[5-(4-fluorophenyl)-3-(1-methylethyl)-1-phenyl-1H-pyrazol-4-yl]ethenyl]hydroxyphosphinyl]-3-hydroxybutanoic acid, dilithium salt;

(S)-4-[[2-[5-(4-fluorophenyl)-3-(1-methylethyl)-1-phenyl-1H-pyrazol-4-yl]ethyl]methoxyphosphinyl]-3-hydroxybutanoic acid, methyl ester;

(S)-4-[[2-[5-(4-fluorophenyl)-3-(1-methylethyl)-1-phenyl-1H-pyrazol-4-yl]ethyl]hydroxyphosphinyl]-3-hydroxybutanoic acid, dilithium salt;

(S)-4-[[2-[3-(4-fluorophenyl)-5-(1-methylethyl)-1-phenyl-1H-pyrazol-4-yl]ethyl]methoxyphosphinyl]-3-hydroxybutanoic acid, methyl ester;

(S)-4-[[2-[3-(4-fluorophenyl)-5-(1-methylethyl)-1-phenyl-1H-pyrazol-4-yl]ethyl]hydroxyphosphinyl]-3-hydroxybutanoic acid, dilithium salt;

(S)-4-[[2-[3-(4-fluorophenyl)-5-(1-methylethyl)-1-phenyl-1H-pyrazol-4-yl]ethynyl]methoxyphosphinyl]-3-hydroxybutanoic acid, methyl ester;

(S)-4-[[2-[3-(4-fluorophenyl)-5-(1-methylethyl)-1-phenyl-1H-pyrazol-4-yl]ethynyl]hydroxyphosphinyl]-3-hydroxybutanoic acid, dilithium salt;

(S)-4-[[[4-(4-fluorophenyl)-1-(1-methylethyl)-3-phenyl-1H-pyrazol-5-yl]ethynyl]methoxyphosphinyl]-3-hydroxybutanoic acid, methyl ester;

(S)-4-[[[4-(4-fluorophenyl)-1-(1-methylethyl)-3-phenyl-1H-pyrazol-5-yl]ethynyl]hydroxyphosphinyl]-3-hydroxybutanoic acid, dilithium salt;

(S)-4-[[2-[4-(4-fluorophenyl)-1-(1-methylethyl)-3-phenyl-1H-pyrazol-5-yl]ethyl]methoxyphosphinyl]-3-hydroxybutanoic acid, methyl ester;

(S)-4-[[2-[4-(4-fluorophenyl)-1-(1-methylethyl)-3-phenyl-1H-pyrazol-5-yl]ethyl]hydroxyphosphinyl]-3-hydroxybutanoic acid, dilithium salt;

(S)-4-[[[1-(4-fluorophenyl)-4-(1-methylethyl)-2-phenyl-1H-imidazole-5-yl]ethynyl]methoxyphosphinyl]-3-hydroxybutanoic acid, methyl ester;

(S)-4-[[[1-(4-fluorophenyl)-4-(1-methylethyl)-2-phenyl-1H-imidazol-5-yl]ethynyl]methoxyphosphinyl]-3-hydroxybutanoic acid, methyl ester;

(S)-4-[[2-[1-(4-fluorophenyl)-4-(1-methylethyl)-2-phenyl-1H-imidazol-5-yl]ethyl]methoxyphosphinyl]-3-hydroxybutanoic acid, methyl ester;

(S)-4-[[2-[1-(4-fluorophenyl)-4-(1-methylethyl)-2-phenyl-1H-imidazol-5-yl]ethyl]hydroxyphosphinyl]-3-hydroxybutanoic acid, dilithium salt;

(S)-4-[[[2-(cyclohexylmethyl)-4,6-dimethylphenyl]ethynyl]hydroxyphosphinyl]-3-hydroxybutanoic acid or its dilithium salt or methyl ester thereof;

4-[[2-[2-(cyclohexylmethyl)-4,6-dimethylphenyl]ethenyl]hydroxyphosphinyl]-3-hydroxybutanoic acid or its dilithium salt or methyl ester thereof;

(S)-4-[[2-[2-(cyclohexylmethyl)-4,6-dimethylphenyl]ethyl]hydroxyphosphinyl]-3-hydroxybutanoic acid or its dilithium salt or methyl ester thereof;

4-[[[[4'-fluoro-3,3',5-trimethyl[1,1'-biphenyl]-2-yl]oxy]methyl]hydroxyphosphinyl]-3-hydroxybutanoic acid or its dilithium salt or methyl ester thereof;

4-[[[4'-fluoro-3,3',5-trimethyl[1,1'-biphenyl]-2-yl]methyl]hydroxyphosphinyl]-3-hydroxybutanoic acid or its dilithium salt or methyl ester thereof;

(S)-4-[[[1-(4-fluorophenyl)-3-methyl-2-naphthalenyl]ethynyl]hydroxyphosphinyl]-3-hydroxybutanoic acid or its dilithium salt or methyl ester thereof;

(E)-4-[[2-[1-(4-fluorophenyl)-3-methyl-2-naphthalenyl]ethenyl]hydroxyphosphinyl]-3-hydroxybutanoic acid or its dilithium salt or methyl ester thereof;

(S)-4-[[2-[1-(4-fluorophenyl)-3-methyl-2-naphthalenyl]ethyl]hydroxyphosphinyl]-3-hydroxybutanoic acid or its dilithium salt or methyl ester thereof;

4-[[3-[4'-fluoro-3,3',5-trimethyl[1,1'-biphenyl]-2-yl]propyl]methoxyphosphinyl]-3-hydroxybutanoic acid, methyl ester;

4-[[3-[4'-fluoro-3,3',5-trimethyl[1,1'-biphenyl]-2-yl]propyl]hydroxyphosphinyl]-3-hydroxybutanoic acid, dilithium salt;

[1S-[1α(R*),2α,4αβ,8β,8aα]]-4-[[2-[8-(-2,2-dimethyl-1-oxobutoxy)decahydro-2-methyl-1-naphthalenyl]ethyl]methoxyphosphinyl]-3-hydroxybutanoic acid, methyl ester;

[1S-[1α(R*),2α,4αβ,8β,8aα]]-4-[[2-[8-(-2,2-dimethyl-1-oxobutoxy)decahydro-2-methyl-1-naphthalenyl]ethyl]hydroxyphosphinyl]-3-hydroxybutanoic acid, dilithium salt;

(S)-4-[[[3'-(4-fluorophenyl)spiro]cyclopentane-1,1'-[1H]indene]-2-yl]ethynyl]methoxyphosphinyl]-3-hydroxybutanoic acid, methyl ester; and (S)-4-[[[3'-(4-fluorophenyl)spiro]cyclopentane-1,1'-[1H]indene]-2-yl]ethynyl]hydroxyphosphinyl]-3-hydroxybutanoic acid, dilithium salt.

An exemplary process for forming compounds of formula XIII employing the compounds of formula I where R₁ is —X—Z includes (1) converting the compounds of formula I where R₁ is —X—Z to a compound of formula

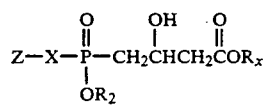

using a reducing agent such as NaBH₄ in an organic solvent such as ethanol;

(2) saponifying formula XIV compounds to the diacid of formula

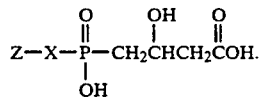

Compounds of formula XV may be further titrated with a base such as sodium hydroxide to produce the preferred final product of formula

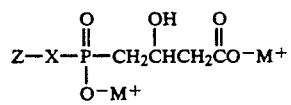

Alternatively, the diacid may be converted to a mono amine salt or mono alkali metal salt (sodium preferred) for the purpose of purification.

An exemplary process for forming compounds of formula XIII employing the compounds of formula I where R₁ is —OR₂' includes reacting compounds of formula I where R₁ is —OR₂' with a reducing agent such as PtO₂ in an organic solvent such as methanol to form the alcohols of formula

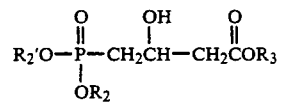

Compounds of formula XVIII may then be converted to compounds of formula XIII as disclosed in U.S. Pat. No. 5,091,378.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

4-[[[1-(4-Fluorophenyl)-3-(1-methylethyl)-1H-indol-2-yl]ethynyl]hydroxyphosphinyl]-3-oxobutanoic acid, ethyl ester, 1-adamantanamine (1:1) salt

A.

[[1-(4-Fluorophenyl)-3-(1-methylethyl)-1-H-indol-2-yl]ethynyl]phosphinic acid, ethyl ester 1. 1-(4-Fluorophenyl)-3-(1-methylethyl)-1H-indol-2-carboxaldehyde a. 4-Methyl-2-oxopentanoic ethyl ester 4-Methyl-2-oxopentanoic acid, sodium salt (25 g) was dissolved in a minimum amount of water, acidified to pH 1 with concentrated hydrochloric acid and then extracted several times with methylene chloride. The aqueous phase was saturated with sodium chloride and back-extracted (twice) with methylene chloride. The combined organic phases were washed with brine, dried over anhydrous sodium sulfate and evaporated in vacuo to give 17.7 g (82.8% recovery) of the free acid as a viscous oil.

A mixture of the acid (17.7 g, 136 mmol) in dry benzene (200 mL) was treated with 1,8-diazobicyclo[5.4.0]undec-7-ene (20.4 mL, 136.2 mmol, 1 eq) giving an exothermic reaction (heat of crystallization) and a gel-like crystalline salt formed. The mixture was treated with ethyl iodide (10.9 mL, 1 eq) and mechanically stirred under argon for three hours. Precipitated salts were removed by filtration, the filtrate was washed once with a small amount of water (50 mL) and brine, then dried over anhydrous sodium sulfate. Benzene was removed by distillation at atmospheric pressure and the yellow liquid remaining was vacuum distilled to give 6.46 g (35.1%) of the title compound as a clear, pale yellow liquid with boiling point equaling 65° C. to 66° C. (5 mm Hg).

b. 4-Methyl-2-(phenylhydrazono)pentanoic acid, ethyl ester

A solution of the title a compound (5 g, 31.6 mmol) in dry methylene chloride (30 mL) was treated with phenylhydrazine (3.3 mL, 33.2 mmol, 1.05 eq) dropwise over five minutes and the yellow mixture stirred under argon at room temperature over 4Å sieves for three hours. The mixture was dried over anhydrous sodium sulfate, filtered and evaporated in vacuo to give 8.105 g of an orange oil. The crude oil was purified by flash chromatography on LPS-1 silica gel (30:1) eluting with (97:3) hexane-ethyl acetate. Product fractions were evaporated to give 6.8 g (86%) of pure title compound and 848 mg (10.8%) of the geometrical isomer of the title compound. Total yield=97.5% c. 3-(1-Methylethyl)-1H-indole-2-carboxylic acid, ethyl ester

Gaseous hydrogen chloride was bubbled (gas dispersion tube) into a dry absolute ethanolic (50 mL, over 3Å sieves) solution of the title b compound (6.8 g, 27.4 mmol) for 30 minutes at room temperature. The exothermic reaction was characterized by color changes from yellow to red to deep green followed by precipitation of white ammonium chloride. The suspension was stirred an additional 20 minutes under Drierite, then dumped into ice cold water (50 mL). Ethanol was removed in vacuo and the residue partitioned between ethyl acetate and water. The aqueous layer was extracted with ethyl acetate (twice), the combined organic phases washed with water and brine, then dried over anhydrous sodium sulfate and evaporated in vacuo to give 4.969 g of a green solid. The crude solid was dissolved in hot hexane, treated with Darco, filtered through packed Celite, concentrated to a 30–50 mL volume and the yellow solution allowed to crystallize. Precipitated crystals were collected by filtration, rinsed with cold hexane and dried to give 4.34 g (68.5%) of pure title compound as white needles with melting point equaling 80° C. to 81° C. TLC (9:1) hexane-acetone, $R_f=0.42$, UV & PMA. $R_f$ of the title b and title c compounds were identical but the title c compound had a bright purple fluorescence.

d. 1-(4-Fluorophenyl)-3-(1-methylethyl)-1H-indole-2-carboxylicacid, ethyl ester

A solution of the title c compound (3.937 g, 17 mmole) and 1-bromo-4-fluorobenzene (9.34 mL, 85 mmole, 5 eq.) in dry dimethyl formamide (15 mL) was treated with cuprous oxide (245 mg, 1.7 mmole, 0.1 eq) and refluxed under argon for 17 hours. Additional bromide (9.34 mL, 5 eq) and cuprous oxide (245 mg, 0.1 eq) were added, refluxing continued for six hours, more cuprous oxide added (730 mg, 5.1 mmol) and refluxing continued for 60 more hours. Dimethyl formamide and excess bromide were distilled off in vacuo and the orange residual oil taken up in ethyl acetate, filtered through packed Celite, washed with saturated sodium bicarbonate and brine, then dried over anhydrous sodium sulfate and evaporated to give 5.385 g (97.2%) of desired crude title compound as an orange oil.

e. 1-(4-Fluorophenyl)-3(1-methylethyl)-1H-indole-2-methanol

To cold (0° C., ice bath), dry ethyl ether (24 mL) under argon was added solid lithium aluminum hydride (907 mg, 23.9 mmol, 1.5 molar eq) followed by dropwise addition of the title d compound (5.185 g, 15.9 mmol) in dry ethyl ether (10 mL) over ten minutes. The mixture was stirred for one hour at 0° C., then quenched at 0° C. by sequential dropwise addition of water (910 µl), 15% sodium hydroxide (910 mL) and water (2.73 mL). The supension was filtered through anhydrous magnesium sulfate over packed Celite and the filtrate evaporated to a clear, colorless oil. The oil gradually crystallized from hexane to give in two crops (3.771 g and 0.333 g) 4.10 g (90.9%) of pure title compound as white, granular crystals with melting point equalling 81° C. to 82° C.

f. 1-(4-Fluorophenyl)-3-(1-methylethyl)-1H-indole-2-carboxaldehyde

A solution of the Dess-Martin periodinane (6.46 g, 15.24 mmol) in dry methylene chloride (30 mL) was treated with dry t-butanol (4Å sieves, 1.44 mL, 15.24 mmol, 1.0 eq) and the mixture stirred under argon for 15 minutes at room temperature. A solution of the title e compound; (3.599 g, 12.7 mmol) in dry methylene chloride (13 mL) was added drop-wise over ten minutes and the pale yellow mixture stirred under argon at room temperature for 30 minutes. The reaction mixture was added to a solution of sodium thiosulfate (14.06 g 89 mmol, 7 eq) in freshly prepared 1N sodium bicarbonate (40 mL) and stirred for ten minutes. The aqueous phase was drawn off, the organic phase washed with 1.0N sodium bicarbonate (twice), water, and brine, then dried over anhydrous sodium sulfate and evaporated in vacuo to give 3.877 g of a yellow oil. The crude oil was purified by flash chromatography on LPS-1 silica gel (40:1) eluting with (40:1) Hexane-ethylene oxide. Product fractions were evaporated to give 3.118 g (87.3%, crude yield) of product plus an impurty (same $R_f$ as product). One recrystallization from hot hexane gave 2.643 g (74%, 76% corrected yield based on recovered alcohol) of pure title compound as white fluffy needles with melting point equalling 114° C. to 116° C.

2. 2-(2,2-Dibromoethenyl)-1-(4-fluorophenyl)-3-(1-methylethyl)-1H-indole

To a solution of the title 1 compound (98.4 g, 0.35 mol) and carbon tetrabromide (243.6 g, 2.1 eq, 0.735 mol) in 750 mL methylene chloride was added dropwise a solution of triethyl phosphite (1.47 mol, 4.2 eq, 252 mL) in 100 mL methylene chloride with mechanical stirring over a period of 45 minutes to one hour. During the additon, the internal temperature was maintained between −37° C. to −25° C. After the addition was complete, the reaction temperature was raised to −20° C. over a 30 minute period and then poured into 250 mL saturated sodium bicarbonate and 100 g ice. At the 30 minute period, the TLC indicated that the reaction was over. Hexane:ethyl acetate; 96:4; silica gel; PMA, UV and iodine visualization; $R_f$ 0.35 (s.m.); 0.75 (product).

The organic layer was separated and the aqueous layer was extracted with methylene chloride (300 mL×1). The combined organic layer was washed with saturated sodium bicarbonate (200 mL×2), half saturated sodium chloride (200 mL×2; to remove the possible remaining sodium bicarbonate from the organic layer), brine (200 mL×2) and dried over magnesium sulfate. The organic layer was filtered and concentrated on a rotavap. The crude reaction product is a mixture of liquid and solid. The residue thus obtained was dissolved in 180 mL acetonitrile by heating on a steam bath with occasional shaking. It was left at room temperature for four hours and then in the cold room overnight. The crystal mass was filtered and washed with cold hexane (100 mL) to give 127 g (80%) of the title compound. This material was recrystallized from hexane (3.5 mL/g) to provide 113 g of the title compound in 74% yield (from the title A compound). Recrystallization yield is based on the first crop; m.p. 121° C. to 123.5° C.

3. 2-Ethynyl-1-(4-fluorophenyl)-3-(1-methyethyl)-1H-indole

To a mechanically stirred solution of the title 2 compound (21 g, 48 mmol) in 144 mL toluene at 0° C. was added dropwise a toluene solution of potassium tert-amylate (30.1 mL, 1.13 eq, 54.2 mmol) over a period of 20 minutes, maintaining the internal temperature at ~5° C. After the addition was complete, TLC (silica gel; Toluene:Hexane, 1:9. $R_f$=0.36 for bromoacetylene, 0.3 for the title 2 compound) showed complete elimination of the title 2 compound to the bromoacetylene.

Methanol (9.71 mL, 5 eq, 240 mmol) and dimethyl phosphite (5.72 mL, 1.3 eq, 62.4 mmol) were added sequentially to the reaction mixture, which was then cooled to 0° C. The addition of the initial one-tenth amount of methanol and dimethyl phosphite was exothermic and the order of addition was important to prevent the Arbuzov reaction. Methanol was added before the addition of dimethyl phosphite. A toluene solution of potassium tertamylate (28 mL, 1.05 eq, 50.4 mmol) was added dropwise to the yellow and cloudy solution over a period of 30 minutes while maintaining the internal temperature at ~5° C. The solution became light yellow and cloudy at the end of the addition. After the addition was complete, the reaction was stirred at ~5° C. for an additional 20 minutes (TLC: silica gel; Toluene:Hexane, 1:9. $R_f$=0.36 for bromoacetylene, 0.3 for the title 2 compound). The light yellowish solution was poured into ice-cold saturated ammonium chloride (200 mL). The organic layer was washed with water (100 mL×2), saturated sodium bicarbonate (100 mL×2), half-saturated sodium chloride (100 mL×2), and brine (100 mL×1) and dried over magnesium sulfate.

Following filtration and concentration, hexane (30 mL) was added to the residue to azeotropically remove the trace toluene and the residue became a grey solid. The solid residue was dissolved in 50 mL hexane (~45° C.) Then it was filtered through a silica gel (8 g) and Celite cake. The height of the silica gel in a 2×1¾ inches filter funnel was 0.4 inches. On top of this silica gel another 0.4 inches Celite was added before filtering the solution. The cake was washed with an additional 45 mL hexane. The total volume of the solution was reduced to two-thirds under reduced pressure and then it was seeded and set aside at room temperature for one hour and at 4° C. overnight. The solution was decanted and the crystals were washed with cold hexane (5 mL×2). After drying, 10.5 g of the title compound was obtained as a white solid (80%).

4. [[1-(4-Fluorophenyl)-3-(1-methylethyl)-1-H-indol-2-yl]ethynyl]phosphinic acid, ethyl ester To a solution of the title 3 compound (110 g, 0.397 mol) in dry tetrahydrofuran at −72° C. (acetone and dry ice bath) under an argon atmosphere with mechanical stirring, a 2.60M hexane solution of n-butyllithium (150.6 mL, 0.391 mol) was added dropwise over a 50 minute period while maintaining the reaction temperature at approximately −75° C. The resulting solution was stirred between −70° C. and −75° C. for an additional 15 minutes. Freshly distilled diethyl chlorophosphite (66 mL, 0.46 mol) was added dropwise (syringe) over ten minutes to the above solution. The resultant solution was stirred between −71° C. and −75° C. for approximately 20 minutes and was then quenched with a saturated sodium bicarbonate solution (250 mL) and allowed to warm to room temperature. The starting material appeared gone by TLC (10% toluene/hexane). In a more polar solvent system (18:1:1 dichloromethane:acetic acid:methanol) the desired ethyl phosphinite was seen due to hydrolysis on the silica gel ($R_f$ approximately 0.8) as well as a small amount of the phosphinic acid ($R_f$ approximately 0.15).

The mixture was diluted with distilled water (330 mL) and ethyl acetate (670 mL). The aqueous phase was removed and extracted with ethyl acetate (350 mL×1). The organic phases were then combined, washed with a half-saturated sodium chloride solution (400 mL×2), brine (400 mL×1), dried over anhydrous sodium sulfate, and filtered. The filtrate was concentrated at reduced pressure to approximately half of its original volume (approximately 1 liter). Deionized water (8 mL) and para-toluenesulfonic acid (1.47 g, 0.008 mol) were added to the concentrated solution at room temperature, and the resultant solution was stirred for approximately ten minutes. This hydrolysis was monitored by TLC (10% toluene/hexane) in which the intermediate phosphite could be observed ($R_f$ approximately 0.50) along with an unknown impurity ($R_f$ approximately 0.58; trace amount). The resultant solution was washed with a saturated sodium bicarbonate solution (100 mL×2), brine (100 mL×1), dried over anhydrous sodium sulfate, and concentrated to dryness at reduced pressure to obtain approximately 178 g of a dark, brown oil. This oil was dissolved in diethyl ether (115 mL) and diluted with hexane (300 mL). The ether was then removed in vacuo until a cloudy, white precipitate was seen forming. The mixture was kept at room temperature for approximately ten minutes (some crystal formation was observed) and then in the cold room (4° C.) for approximately 12 hours. The resultant crop was filtered, and the crystals were washed with cold 2% ethyl acetate in hexane (200 mL) and dried under vacuum (approximately 1 mm Hg) to give the title compound as a beige solid in 76% yield (110.9 g); m.p. 80° C. to 82.5° C. 35 g of a second crop of crystals consisting of an approximately 1:1 mixture of the product and the phosphinic acid (proton NMR) along with another minor unknown impurity was obtained from the mother liquor.

B.

(Z)-3-Ethoxy-4-[[[1-(4-fluorophenyl)-3-(1-methylethyl)-1H-indol-2-yl]ethynyl]hydroxyphosphinyl]-2-butenoic acid, ethyl ester Under argon, trimethylsilyl chloride (7.2 mL, 6.18 g, 56.9 mmol) was added to a 0° C. solution of the title A compound (20.0 g, 54.2 mmol) and triethylamine (8.0 mL, 5.75 g, 56.9 mmol) in chloroform (160 mL). The temperature was kept below 5° C. during the addition. After stirring at room temperature for 15 minutes, bis(-trimethyl-silyl) trifluoroacetamide (14.8 mL, 14.6 g, 56.9 mmol) was added and the solution stirred for an additional 15 minutes. Distilled ethyl 4-bromo-3- ethoxy-2-butenoate (24.7 g, 94.8 mmol) was added and the solution refluxed for ten hours.

After cooling to room temperature, the reaction was quenched by adding methanol (6.5 mL, 84.9 mmol). After concentration, the residual syrup was partitioned between diethyl ether (400 mL) and 5% aqueous hydrochloric acid (200 mL). After extraction, the ethereal phase was washed with saturated sodium chloride (200 mL), dried with sodium sulfate, filtered, and concentrated to an orange gum (37 g). The crude material (37 g) was purified by flash chromatography (1.1 kg, Merck Kieselgel 60) eluting with dichloromethanemethanol-acetic acid (18:1.5:0.5). The appropriate fractions were combined, concentrated, and azeotroped with heptane to remove the residual acetic acid. The resulting syrup was dissolved in ethyl acetate (100 mL) and filtered through celite to remove any silicates. Concentration afforded the title compound (17.7 g, 65.8%) as an orange solid. $R_f=0.55$.

C.

4-[[[1-(4-Fluorophenyl)-3-(1-methylethyl)-1H-indol-2-yl]ethynyl]hydroxyphosphinyl]-3-oxobutanoic acid, ethyl ester, 1-adamantanamine (1:1) salt A solution of the title B compound (3.1 g, 6.23 mmol) in acetic acid-water (3:1, 36 mL) was heated at 50° C. for six hours. After cooling to room temperature, the solution was diluted with diethyl ether (300 mL) and extracted with saturated brine (200 mL). The ethereal phase was washed with water (150 mL), then saturated brine (200 mL), dried (magnesium sulfate), filtered, coevaporated with heptane (2×25 mL), and then coevaporated with toluene (5×50 mL) to afford the intermediate phosphinic acid as a red oil (3.3 g).

A filtered solution of 1-adamantanamine (1.0 g, 6.26 mmol) in diethyl ether (20 mL) was added to a solution of the above phosphinic acid (3.3 g) in diethyl ether (20 mL). The combined solution was concentrated to approximately 5 mL and left to crystallize at +5° C. for 24 hours. After filtration, the solids were washed with cold (+5° C.) diethyl ether (5×5 mL) and dried (3 hours, 0.01 mm Hg) to afford the crude adamantanamine salt (2.23 g, 59%) as a tan solid.

The crude adamantanamine salt (10.7 g) was suspended in ethanol (25 mL) and heated to afford dissolution. After cooling to room temperature, the solution was seeded and left at +5° C. for two hours, then at −20° C. for 16 hours. Filtration afforded the purified adamantanamine adduct (7.4 g).

Three grams (3.0 g) of the remaining crude salt was recrystalized to afford an additional 2.3 g of purified material.

The mother liquors from both recrystallizations were combined and concentrated to a syrup. Diisopropyl ether (5 mL) was added, and after one hour, the solids (1.8 g) were filtered and recrystalized from ethanol (3.5 mL) as described above to afford an additional 1.4 g of purified material.

The combined three batches were dried (four hours, 50° C., 0.01 mm Hg) to afford the title compound (11.0 g, 80% recovery, 51% yield) as a white solid.

EXAMPLE 2

4-[[[1-(4-Fluorophenyl)-3-(1-methylethyl)-1H-indol-2-yl]ethynyl]hydroxyphosphinyl]-3-oxobutanoic acid, ethyl ester, 1-adamantanamine (1:1) salt

A. (Z)-4-chloro-3-ethoxy-2-butenoic acid, ethyl ester

A mixture of ethyl-4-chloroacetoacetate (5.0 g), triethyl orthoformate (4.5 g) and concentrated sulfuric acid (2 drops) was stirred at room temperature for 48 hours under a nitrogen atmosphere. The excess triethyl orthoformate was removed on a rotavap and the residue was dissolved in toluene (~20 mL) and a small amount of p-toluene sulfonic acid was added and refuxed for three hours. The mixture was diluted with ethyl acetate (~20 mL) and washed with aqueous sodium bicarbonate and brine; dried over anhydrous sodium sulphate and the solvent removed on a rotavap to obtain the title compound.

B.

(Z)-3-Ethoxy-4-[ethoxy[[1-(4-fluorophenyl)-3-(1-methylethyl)-1H-indol-2-yl]ethynyl]-phosphinyl]-2-butenoic acid, ethyl ester To a solution of the title A compound of Example 1 (0.25 g, 0.68 mmol) in toluene (1 mL) under an argon atmosphere at 0° C. was added triethylamine (0.1 mL, 0.71 mmol) followed by trimethylsilyl chloride (0.09 mL, 0.71 mmol). After stirring the reaction mixture for 15 minutes at 0° C., it was brought to ambient temperature and bis-trimethylsilyl trifluoroacetamide (0.19 mL, 0.71 mmol) was added to it. The reaction mixture was stirred at ambient temperature for 15 minutes. The title A compound (0.25 g, 1.17 mmol) was added and the reaction mixture refuxed for 24 hours. The reaction was cooled, diluted with ethyl acetate (~10 mL) and washed with water, brine and dried over anhydrous sodium sulphate The crude product obtained after the evaporation of the solvent was purified by column chromatography over silica gel using ethyl acetate hexane as the solvent system to obtain the title compound (0.095 g, 28%).

C.

(Z)-3-Ethoxy-4-[[[1-(4-fluorophenyl)-3-(1-methylethyl)-1H-indol-2-yl]ethynyl] hydroxyphosphinyl]-2-butenoic acid, ethyl ester To a solution of the title B compound (5 g) in methylene chloride (50 mL) was added N,O-bis(trimethylsilyl)trifluoroacetamide (6.4 mL) and trimethylsilyl bromide (5.8 mL) over a period of 30 minutes. The reaction was stirred overnight at room temperature and then concentrated to a syrup on a rotary evaporator. It was dissolved in ethyl acetate (100 mL) and washed with hydrochloric acid (10%; 1×25 mL), water (1×25 mL) and brine (25 mL) and dried over amhydrous sodium sulfate. The solvent was removed on a rotary evaporator at ~30° C. to get the product as glassy material (4.5 g).

D.

4-[[[1-(4-Fluorophenyl)-3-(1-methylethyl)-1H-indol-2-yl]ethynyl]hydroxyphosphinyl]-3-oxobutanoic acid, ethyl ester, 1-adamantanamine (1:1) salt A solution of the title C compound (3.1 g) in acetic acid-water (3:1, 36 mL) was heated at 50° C. for six hours. After cooling to room temperature, the solution was diluted with diethyl ether (300 mL) and extracted with saturated brine (200 mL). The ethereal phase was washed with water (150 mL), then saturated brine (200 mL), dried (Magnestium sulfate), filtered, coevaporated with heptane (2×25 mL), and then coevaporated with toluene (5×50 mL) to afford the intermediate phosphinic acid as a red oil (3.3 g).

A filtered solution of 1-adamantanamine (1.0 g) in diethyl ether (20 mL) was added to a solution of the above phosphinic acid (3.3 g) in diethyl ether (20 mL). The combined solution was concentrated to approximately 5 mL and left to crystallize at +5° C. for 24 hours. After filtration, the solids were washed with cold (+5° C.) diethyl ether (5×5 mL) and dried (3 h, 0.01 mm Hg) to afford the crude adamantanamine salt (2.23 g, 59%, Hl 90) as a tan solid.

EXAMPLE 3

4-[Ethoxy[[1-(4-fluorophenyl)-3-(1-methylethyl)-1H-indol-2-yl]ethynyl]phosphinyl]-3-oxobutanoic acid, ethyl ester A. 4-Chloro-3-[(trimethylsilyl)oxy]-2-butenic acid, ethyl ester To a solution of ethyl 4-chloro-3-oxobutanoate (30 g, 0.183 mol, 24.7 mL) and trimethylsilyl chloride (30.2 mL, 0.234 mol) in tetrahydrofuran (360 mL) was added dropwise triethylamine (30.61 mL, 0.23 mol) at −20° C. with mechanical stirring. After the addition was complete (~15 minutes), the mixture was stirred for an additional 30 minutes at −20° C., 30 minutes at 0° C., and then one hour at room temperature. The reaction was diluted with a large excess of hexane (1 L). The resulting precipitate was filtered and the solution was concentrated on a rotavap to an oily residue. It was diluted with hexane (400 mL), filtered and the filtrate was concentrated on a rotavap to an oily residue. This process was repeated until no further precipitation occurred. Distillation of the residue (b.p. 70° C. to 78° C./1 mm Hg) gave the title compound (33 g, 80%) as a mixture of cis,trans isomers.

B.
4-[Ethoxy[[1-(4-fluorophenyl)-3-(1-methylethyl)-1H-indol-2-yl]ethynyl]-phosphinyl]-3-oxobutanoic acid, ethyl ester To a solution of the title A compound of Example 1 (0.2 g, 0.59 mmol) in chloroform (4 mL) in a 25 mL round bottom flask under argon atmosphere at 0° C. was added triethylamine (0.09 mL, 0.65 mmol) followed by trimethylsilyl chloride (0.08 mL, 0.65 mmol). After stirring the reaction mixture for 15 minutes at 0° C., it was brought to room temperature. In a separate round bottom flask the title A compound (0.15 g, 0.65 mmol) was dissolved in chloroform (1 mL) and bis-trimethylsilyl trifluoroacetamide (0.19 mL, 0.7 mmol) was added to it. This solution was added via a cannula to the phosphite solution and the reaction mixture refluxed overnight to form an adduct intermediate. The reaction mixture was cooled to room temperature, diluted with ethyl acetate (~10 mL) and washed with water, brine and dried over anhydrous sodium sulfate to give the crude ketone which was purified by column chromatography to get the pure material in (0.024 g, ~10%).

EXAMPLE 4

4-[[[1-(4-Fluorophenyl)-3-(1-methyethyl)-1H-indol-2-yl]ethynyl]methoxyphosphinyl]-3-oxobutanoic acid, ethyl ester A. (Z)-4-Iodo-3-[(trimethylsilyl)oxy]-2-butenoic acid, ethyl ester Sodium iodide (228 g) was dissolved in acetone (135 mL) and cooled to 0° C. 4-chloro-3-oxobutanoic acid, ethyl ester (5.0 g) was added to the sodium iodide solution and the mixture was stirred at 0° C. for 20 minutes It was diluted with pentane (135 mL) and water (135 mL). The reaction mixture was diluted with ethyl acetate and washed with water, brine and dried over anhydrous sodium sulfate to give an intermediate (4-Iodo-3-oxobutanoic acid, ethyl ester; 6.2 g yield).

The intermediate (6.22 g, 24.29 mmol) and tetrahydrofuran (60 mL) were combined in a 3-necked round bottom flask under an argon atmosphere. Trimethylsilyl chloride (3.77 mL, 29.7 mmol) was added to the solution and cooled to −20° C. Triethylamine (4.14 mL, 29.7 mmol) was added dropwise over a period of 15 minutes. The reaction was allowed to warm to room temperature and GC indicated complete reaction. It was diluted with pentane (60 mL) and filtered through celite. The filtrate was concentrated to an oil and diluted with pentane (60 mL) and filtered through a celite pad. The filtrate was concentrated to an oil. The oil was purified by fractional distillation to give pure title compound (5.0 g, 63%).

B.
4-[[[1-(4-Fluorophenyl)-3-(1-methylethyl)-1H-indol-2-yl]ethynyl]methoxyphosphinyl]-3-oxobutanoic acid, ethyl ester A 2-necked 25 mL round bottom flask was charged with the title A compound of Example 1 (0.25 g, 0.68 mmol) in chloroform (3 mL) and cooled to 0° C. under an argon atmosphere. To the above solution was added triethylamine (0.1 mL, 0.71 mmol) and trimethylsilyl chloride (0.09 mL, 0.71 mmol). The mixture was stirred for 15 minutes at 0° C. and warmed to room temperature. Bistrimethylsilyltrifluoro acetamide was added to the mixture and stirred for 30 minutes at room temperature. The title A compound (0.45 g, 1.36 mmol) was added to the reaction mixture and refluxed for ten minutes. The reaction mixture was treated with 5% hydrochloric acid and diluted with ethyl acetate and washed with water, brine and dried over anhydrous sodium sulfate to obtain the crude acid (0.42 g). Esterification of the crude acid with diazomethane followed by chromatographic purification gave the title compound (116 g, 36%).

EXAMPLE 5

4-[[[1-(4-Fluorophenyl)-3-(1-methylethyl)-1H-indol-2-yl]ethynyl]hydroxyphosphinyl]-3-oxobutanic acid, ethyl ester,1-adamantanamine (1:1) salt A 2-necked 50 mL round bottom flask was changed with the title A compound of Example 1 (1.0 g, 2.71 mmol) in chloroform (10 mL) and cooled to 0° C. under an argon atmosphere. To the above solution was added triethylamine (0.4 mL, 2.8 mmol) and trimethylsilyl chloride (0.36 mL, 28 mmol). The mixture was stirred for 15 minutes at 0° C. and warmed to room temperature. It was stirred at room temperature for 30 minutes and the bistrimethylsilyl trifluoroacetamide (0.75 mL, 2.8 mmol) was added to it and stirred an additional 30 minutes at room temperature. The reaction mixture was heated to refux and then the title A compound of Example 4 (1.3 g, 4.2 mmol) was added dropwise over five minutes. The reaction was heated for 30 minutes then diluted with ethyl acetate and washed with water, brine and dried over anhydrous sodium sulfate to obtain the crude acid (1.44 g). The crude acid was dissolved in diethylether (10 mL) and treated with 1-adamantanamine (0.26 g). It was kept in the freezer overnight and filtered to obtain the 1-adamantanamine salt of the phosphinic acid (0.54 g, 32%).

EXAMPLE 6

4-[[[1-(4-Fluorophenyl)-3-(1-methylethyl)-1H-indol-2-yl]ethynyl]hydroxylphosphinyl]-3-hydroxybutanoic acid, ethyl ester, 1-adamantanamine (1:1) salt Sodium borohydride (50 mg) was added to a solution of the crude title compound of Example 4 (325 mg, 0.64 mmol) in ethanol (5 mL). After stirring for 30 minutes, the solution was concentrated to remove the ethanol. The syrup was dissolved in ether (20 mL) and extracted with 10% aqueous hydrochloride acid (5 mL). The ethereal phase was then washed with water (5 mL) and with brine (5 mL), then dried (magnesium sulfate), filtered, and concentrated to a syrup which was applied to a silica gel column. Elution using hexanes-ether (2:1, 1:1, then 1:4) followed by concentration of the appropriate fractions afforded the 3-hydroxy derivative (150 mg, 48% two-steps including Example 4-step, a clear oil) as an intermediate.

Bromotrimethylsilane (0.08 mL, 0.61 mmol) was added to a solution of the 3-hydroxy derivative intermediate (150 mg) and bistrimethylsilyltrifluoroacetamine (0.11 mL, 0.42 mmol) in dichloromethane (5 mL). After stirring for two hours at room temperature, ether (15 mL) was added and the solution extracted with 0.5% aqueous hydrochloride acid, water (5 mL), and with brine (5 mL). The organic phase was then dried (magnesium sulfate), filtered, concentrated to a syrup, and then dissolved in ether (5 mL).

A filtered solution of 1-adamantanamine (47 mg, 0.34 mmol) in ether (5 mL) was added to the above solution of the phosphinic acid. After one hour, the mixture was filtered and the solids washed with ether (5 mL) then dried (magnesium sulfate) to afford the title compound (112 mg, 58%) as a white solid.

EXAMPLE 7

4-(Diethoxyphosphinyl)-3-oxobutanoic acid, ethyl ester

The title A compound of Example 3 (41.0 g, 0.174 mol) was dissolved in (EtO)$_3$P (150 mL, 0.87 mol) and heated at 115° C. (bath temperature) for 18 hours and then cooled to room temperature. The excess (EtO)$_3$P was distilled off at reduced pressure (1 mm Hg, 45° C. bath temperature). The resulting brown residue was purified by chromatography on silica gel, isopropanol:-hexane (1:9), to give the title compound as a pale yellow liquid (31 g, 67%).

EXAMPLE 8

4-(Dimethoxyphosphinyl)-3-oxobutanoic acid, methyl ester

A. (Z)-4-Chloro-3-[(trimethylsilyl)oxy]-2-butenoic acid, methyl ester

A solution of 4-chloro-3-oxobutanoic acid, methyl ester (60.4 g, 0.4 mol) and trimethylsilyl chloride (48.8 mL, 1.3 mol) in 500 mL dry ethyl acetate was cooled to −20° C. and triethylamine (17.42 mL, 1.25 mol) was added dropwise over 15 minutes under nitrogen atmosphere. The cold bath was removed and the heterogeneous mixture was stirred for two hours. The mixture was diluted with 200 mL dry hexane, stirred for five minutes and filtered under nitrogen. The filtrate was evaporated under vaccum. The product was redissolved in 100 mL hexane and filtered to remove a small amount of TEA.HCl. The filtrate was evaporated and the product was kept under pump vaccum for 0.5 hours to give the title compound (83.95 g, 94%).

B. 4-(Dimethoxyphosphinyl)-3-oxobutanoic acid, methyl ester

A mixture of the title A compound (83.9 g, 0.378 mol), bissilylacetamide (15.23 g, 0.075 mol) and trimethylphosphite (200 g, 1.61 mol) was refluxed (oil bath temp. 125° C.) under argon for 15 hours. TLC, silica gel, 10 methanol/ethyl acetate R$_f$=0.39, (UV and 4,4'-bis-dimethylaminobenzhydrol/heat). The reaction mixutre was cooled to 70° C., volatile components were distilled at 10 mm pressure, and then the product was kept at 0.5 mm pressure for ten minutes. The product was taken up in 250 mL ethyl acetate and washed with brine (2×50 mL), aqueous sodium bicarbonate (25 mL, vigorous reaction) and brine. The organic phase was dried (magnesium sulfate) and the solvent was removed under vaccum to give 55.79 g of the crude title compound. The product was heated to 100° C. under vaccum (0.4 mm) for five minutes to remove the more volatile impurities. The product was cooled, dissolved in 200 mL ethyl acetate, and treated with charcoal, and filtered through a pad of Celite. The filtrate was evaporated to give 43.01 g (yield 51% uncorrected) of the title compound

EXAMPLE 9

4-(Diethoxyphosphinyl)-3-hydroxybutanoic acid, ethyl ester

The title compound of Example 7 (17 g, 63.8 mmol) was dissolved in 200 mL of methanol. To this solution was added PtO$_2$ (1.7 g, 10% w/w). The mixture was degassed by evacuation of air, then refilling with hydrogen. This degassing procedure was repeated three times. The pressure in the Parr-shaker was set to 50 psi, and the mixture was shaken for 36 hours. The catalyst was filtered through a Celite pad and the filtrate was concentrated on a rotavap to give 17.3 g (~100%) of the title compound as a white solid, m.p. 33° C. to 35° C.

EXAMPLE 10

4-(Diethoxyphosphinyl)-3-[[(1,1-dimethylethyl)diphenylsilyl]oxy]butanoic acid, ethyl ester The title compound of Example 9 (4.0 g, 0.0177 mol) was dissolved in 35 mL DMF and treated with imidazole (6.20 g, 0.0912 mol), DMAP (0.1 g, 0.82 mmol) and t-butyldiphenyl chlorosilane (5.6 g). After 24 hours 1.5

L ethyl acetate was added and the solution was washed with 950 mL 1N hydrochloric acid. The aqueous layer was extracted with 30 mL ethyl acetate and the combined organic extracts were washed once with 25 mL 1N hydrochloric acid, four times with 25 mL water, and then with 25 mL brine. The organic layer was dried (magnesium sulfate) and the solvent was removed to give 5.98 g of crude silyl ether The product was pruified by chromatography over silica gel K-60 (95 g, column made in hexane, elution with 120 mL hexane, 100 mL 33% ethyl acetate/hexane, and then 1.2 L 50% ethyl acetate/hexane; 45 mL fractions). Fraction collection was started during elution with the last solvent system. TLC homogeneous fractions were combined and the solvent was removed completely under vacuum to furnish 6.4 g (74%) of the title compound.

EXAMPLE 11

4-(Dimethoxyphosphinyl)-3-[[(1,1-dimethylethyl)-diphenylsilyl]oxy]butanoic acid, methyl ester $PtO_2$ (2.0 g) was added to a solution of the title compound of Example 8 (40.8 g, 0.182 mol) in 200 mL methanol and hydrogenated in a Parr-shaker at 58 psi for 15 hours. The hydrogen pressure fell to 42 psi; the pressure was increased to 58 psi. After 7 hours (4 psi decrease in pressure) the mixture was filtered through Celite, the catalyst was washed with ethyl acetate, and the solvent was evaporated to furnish 39.26 g of crude carbinol intermediate. The intermediate (40.0 g, 0.177 mol) was dissolved in 350 mL DMF and treated with imidazole (62.0 g, 0.912 mol), DMAP (1.0 g, 8.2 mmol) and t-butyldiphenyl chlorssilane (55.94 g, 0.204 mol). After 24 hours 1.5 L ethyl acetate was added and the solution was washed with 950 mL 1N hydrochloric acid. The aqueous layer was extracted with 300 mL ethyl acetate and the combined organic extracts were washed once with 250 mL 1N hydrochloric acid, four times with 250 mL water, and then with 250 mL brine. The organic layer was dried (magnesium sulfate) and the solvent was removed to give 5.98 g of crude silyl ether. The product was pruified by chromatography over silica gel K-60 (950 g, column made in hexane, elution with 1.2 L hexane, 1 L 33% ethyl acetate/hexane, and then 12 L 50% ethyl acetate/hexane; 45 mL fractions). Fraction collection was started during elution with the last solvent system. TLC homogeneous fractions were combined and the solvent was removed completely under vacuum to furnish 64.018 g (74%) of the title compound.

What is claimed is:

1. A method for preparing a compound of the formula

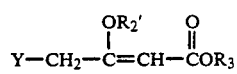

or salt thereof where $R_1$ is —X—Z and X is —C≡C—,
$R_2$ is hydrogen, alkyl or trialkylsilyl;
$R_3$ is hydrogen or alkyl; and
Z is a hydrophobic anchor which is

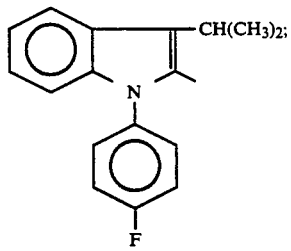

comprising the step of:

(A) reacting a compound of formula

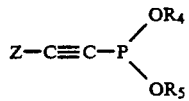

where $R_4$ is alkyl, cycloalkyl or aryl; and $R_5$ is trialkylsilyl or triarylsilyl with a compound of formula

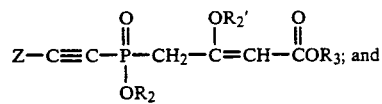

where Y is a halogen and $R_2'$ is hydrogen, alkyl or trialkylsilyl, to form a compound of formula

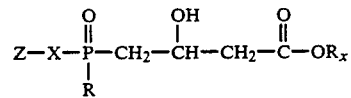

(B) hydrolyzing the product of step (A) to obtain the compounds of formula I.

2. A process for the preparation of a compound of formula

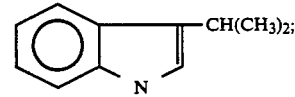

or a salt thereof where

X is —$CH_2$—, —$CH_2CH_2$—, —$CH_2CH_2CH_2$—, —$CH_2$=$CH_2$—, —C≡C—, —$CH_2$O—(where O is linked to Z);

Z is a hydrophobic anchor which

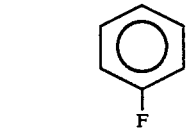

R is hydroxy or lower alkyl; and
$R_x$ is hydrogen or lower alkyl;
comprising the steps of:

(A) preparing a compound of formula

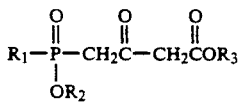
or a salt thereof wherein $R_1$ is —X—Z and X is —C≡C—, $R_2$ is hydrogen, alkyl or trialkylsilyl; $R_3$ is hydrogen or alkyl; and
(B) converting said compound of formula I or a salt thereof to a compound of formula XIII or a salt thereof, with the proviso that said compound of formula I or a salt thereof is prepared by the process of claim 1.
* * * * *